United States Patent
Lazic

(10) Patent No.: US 10,863,991 B2
(45) Date of Patent: Dec. 15, 2020

(54) SURGICAL CLIP MADE OF CARBON FIBER REINFORCED PLASTIC MATERIAL

(71) Applicant: Lazic Besitz GmbH & Co. KG, Tuttlingen (DE)

(72) Inventor: Daniel Lazic, Tuttlingen (DE)

(73) Assignee: LAZIC BESITZ GMBH & CO KG, Tuttlingen (DE)

( * ) Notice: Subject to any disclaimer, the term of this patent is extended or adjusted under 35 U.S.C. 154(b) by 172 days.

(21) Appl. No.: 16/138,974

(22) Filed: Sep. 22, 2018

(65) Prior Publication Data

US 2019/0090880 A1 Mar. 28, 2019

(30) Foreign Application Priority Data

Sep. 28, 2017 (EP) .................................... 17193622

(51) Int. Cl.
*A61B 17/122* (2006.01)
*A61B 17/00* (2006.01)
(Continued)

(52) U.S. Cl.
CPC .......... *A61B 17/1227* (2013.01); *A61L 31/06* (2013.01); *A61L 31/126* (2013.01);
(Continued)

(58) Field of Classification Search
CPC ........ A61B 17/1227; A61B 2017/0092; A61B 2017/00964; A61L 31/06; A61L 31/126
See application file for complete search history.

(56) References Cited

U.S. PATENT DOCUMENTS 4,932,955 A * 6/1990 Merz .................. A61B 17/1227
24/510
8,273,096 B2 9/2012 Lazic
(Continued)

FOREIGN PATENT DOCUMENTS

DE 19935418 C2 7/2001
DE 10 2004 016 859 A1 10/2005
(Continued)

OTHER PUBLICATIONS

Alexander Brack et al., "Development of an artifact-free aneurysm clip", Current Directions in Biomedical Engineering, vol. 2, No. 1, Sep. 30, 2016 (Sep. 30, 2016), pp. 543-546, XP055423361, DOI:10.1515/cdbme-2016-0120.
(Continued)

*Primary Examiner* — Katrina M Stransky
*Assistant Examiner* — Raihan R Khandker
(74) *Attorney, Agent, or Firm* — Hackler Daghighian Martino & Novak

(57) ABSTRACT

An aneurysm surgical clip includes two rotatably interconnected clip parts and a leg spring. The leg spring has two spring legs of which are in each case supported on the two clip parts so as to mutually pretension the two clip parts. The leg spring is formed from a plastics material, in particular PEEK, that is reinforced with continuous carbon fibers. The continuous carbon fibers are aligned along the spring coilings of the leg spring. The two clip parts have in each case one axially projecting protrusion on which the respective spring leg of the leg spring is supported.

10 Claims, 5 Drawing Sheets

(51) Int. Cl.
*A61L 31/06* (2006.01)
*A61L 31/12* (2006.01)
(52) U.S. Cl.
CPC ................ *A61B 2017/0092* (2013.01); *A61B 2017/00964* (2013.01)

(56) References Cited

U.S. PATENT DOCUMENTS

| | | | |
|---|---|---|---|
| 9,585,673 | B2 | 3/2017 | Zieris et al. |
| 2002/0111643 | A1 | 8/2002 | Herrmann et al. |
| 2014/0194908 | A1* | 7/2014 | Lazic ................ A61B 17/083 606/151 |
| 2016/0157867 | A1* | 6/2016 | Zieris ................ A61B 17/1227 606/158 |

FOREIGN PATENT DOCUMENTS

| | | |
|---|---|---|
| DE | 10 2009 003273 A1 | 11/2010 |
| DE | 102013107876 A1 | 1/2015 |
| WO | 2016 107952 A1 | 7/2016 |

OTHER PUBLICATIONS

Alexander Brack et al., "Development of an artifact-free aneurysm clip," Current Directions in Biomedical Engineering, 2(1): 543-546, Sep. 30, 2016, 10.1515/cdbme-2016-0120.

\* cited by examiner

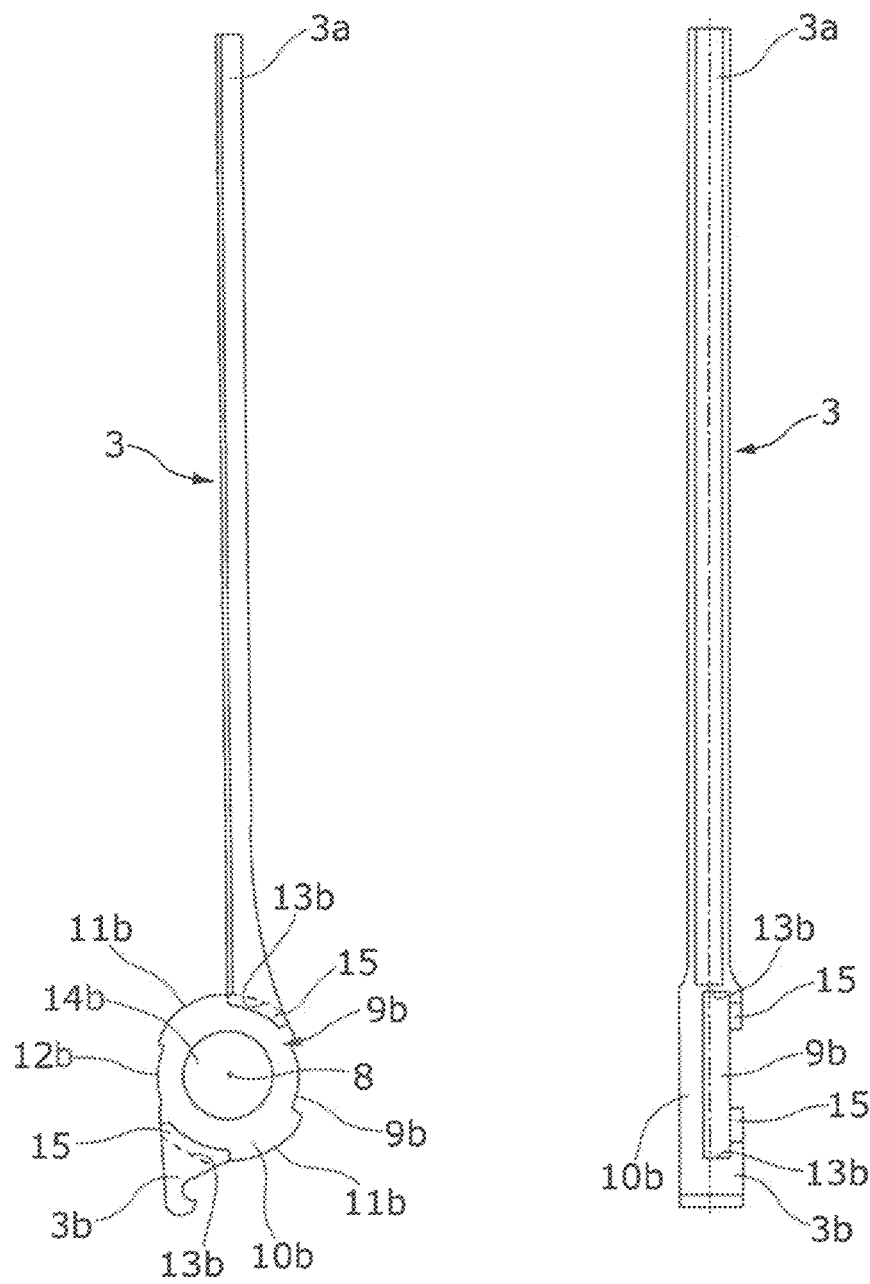

SURGICAL CLIP MADE OF CARBON FIBER REINFORCED PLASTIC MATERIAL

CROSS-REFERENCE TO RELATED APPLICATIONS

This application claims priority to European Patent Application No. 17 193 622.2 filed Sep. 28, 2017, the entire contents of which are hereby incorporated in full by reference.

DESCRIPTION

Field of the Invention

The invention relates to a surgical clip, in particular an aneurysm clip, comprising two rotatably interconnected clip parts and a leg spring, the two spring legs of the which are in each case supported on the two clip parts so as to mutually pretension the two clip parts, wherein the leg spring is formed from a plastics material, in particular PEEK, that is reinforced with continuous carbon fibers, wherein the continuous carbon fibers are aligned along the spring coilings of the leg spring.

Background of the Invention

A surgical clip of this type has become known, for example, by way of Alexander Brack et al., "Development of an artifact-free aneurysm clip", Current Directions in Biomedical Engineering, Vol. 2, No. 1, Sep. 30, 2016, pages 543-546.

Surgical clips comprising two interconnected clip parts made from metal and a leg spring made from metal, the spring legs of which are welded to the clip parts, are known from DE 10 2009 003 273 A1 or DE 10 2004 016 859 A1.

SUMMARY OF THE INVENTION

By contrast, the present invention is based on the object of refining a surgical clip of the type mentioned at the outset such that the leg spring, and in particular the entire clip, are X-ray-transparent.

This object is achieved according to the invention in that the two clip parts comprise in each case one axially projecting protrusion on which the respective spring leg of the leg spring is supported. The protrusion can be configured in a hook-shaped manner so as to radially reach across the respective spring leg and, on account thereof, axially fix the latter, or the respective spring leg can be at least partially embedded in the protrusion in a form-fitting manner, in particular be insert molded.

The leg spring, according to the invention, is produced from an X-ray-transparent fiber-composite material which is composed of PEEK material, which is permitted as an implant material, and of continuous carbon fibers. The continuous carbon fibers are aligned along the spring coilings so as to impart sufficient stability to the leg spring when flexurally stressed.

The two clip parts are particularly preferably also formed from an X-ray-transparent plastics material, in particular PEEK (polyether ether ketone). The two clip parts herein can advantageously be formed from a plastics material, in particular PEEK, that is reinforced with short carbon fibers, thus from an X-ray-transparent fiber-composite material in which the short carbon fibers in the structure are connected to the PEEK in an unorganized manner. In this embodiment the entire clip is formed from an X-ray-transparent material.

In order for the leg spring to be supported on both clip parts, the two spring legs can be connected to the two clip parts in a materially integral manner, in particular be (ultrasonically) welded to one another.

The two clip parts preferably comprise in each case one clamping arm, one operating arm, and one rotary bearing portion located therebetween, said rotary bearing portion having an opening, wherein the rotary bearing portions of the two clip parts are mounted so as to be rotatable within one another, and the openings of the two clip parts form an axial passage opening in which at least some of the spring coilings of the leg spring are disposed.

Preferably, the spring leg is supported on an end face or inner face of the protrusion facing in the force direction of the leg spring or in the rotation direction of the clip, respectively.

Further advantages and advantageous embodiments of the subject matter of the invention can be extracted from the description, the claims and the drawing. The features mentioned above and below may be used individually or collectively in arbitrary combination. The embodiments illustrated and described are not to be understood as exhaustive enumeration but have exemplary character for describing the invention. In the drawing:

BRIEF DESCRIPTION OF THE DRAWINGS

FIGS. 3a, 3b show a second clip part of the clip shown in FIG. 1 in a plan view (FIG. 3a) and in a lateral view (FIG. 3b);

DETAILED DESCRIPTION OF THE PREFERRED EMBODIMENTS

Figure 1:
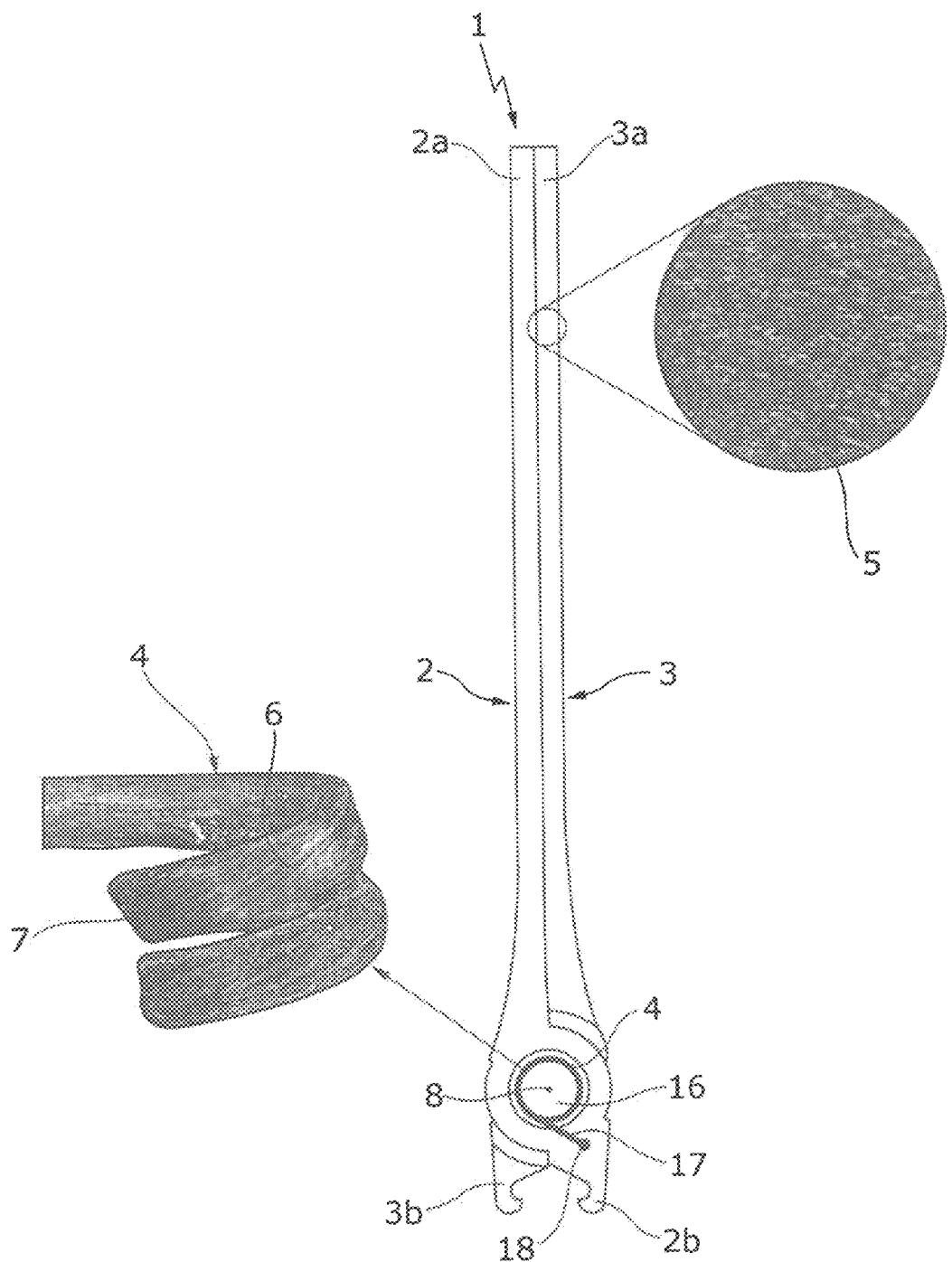
FIG. 1 shows a surgical clip according to the invention, having two clip parts and a leg spring, in the closed end position of said surgical clip.

The surgical clip 1 shown in FIG. 1 comprises two rotatably interconnected scissor-shaped clip parts 2, 3 and a leg spring 4 so as to mutually pretension the two clip parts 2, 3 to the closed end position shown in FIG. 1.

The two clip parts 2, 3 are formed from a PEEK (polyether ether ketone) that is reinforced with short carbon fibers 5, and the leg spring 4 is formed from a PEEK that is reinforced with continuous carbon fibers 6. The clip 1 is thus produced from an X-ray-transparent fiber-composite material which is composed of carbon fibers 5, 6 and PEEK material which is permitted as an implant material. As opposed to the two clip parts 2, 3 in which the short carbon fibers 5 in the structure are connected to the PEEK in an unorganized manner, the continuous carbon fibers 6 in the case of the leg spring 4 are aligned along the spring coilings 7 so as to impart sufficient stability to the leg spring 4 when flexurally stressed.

Figures 2A, 2B:
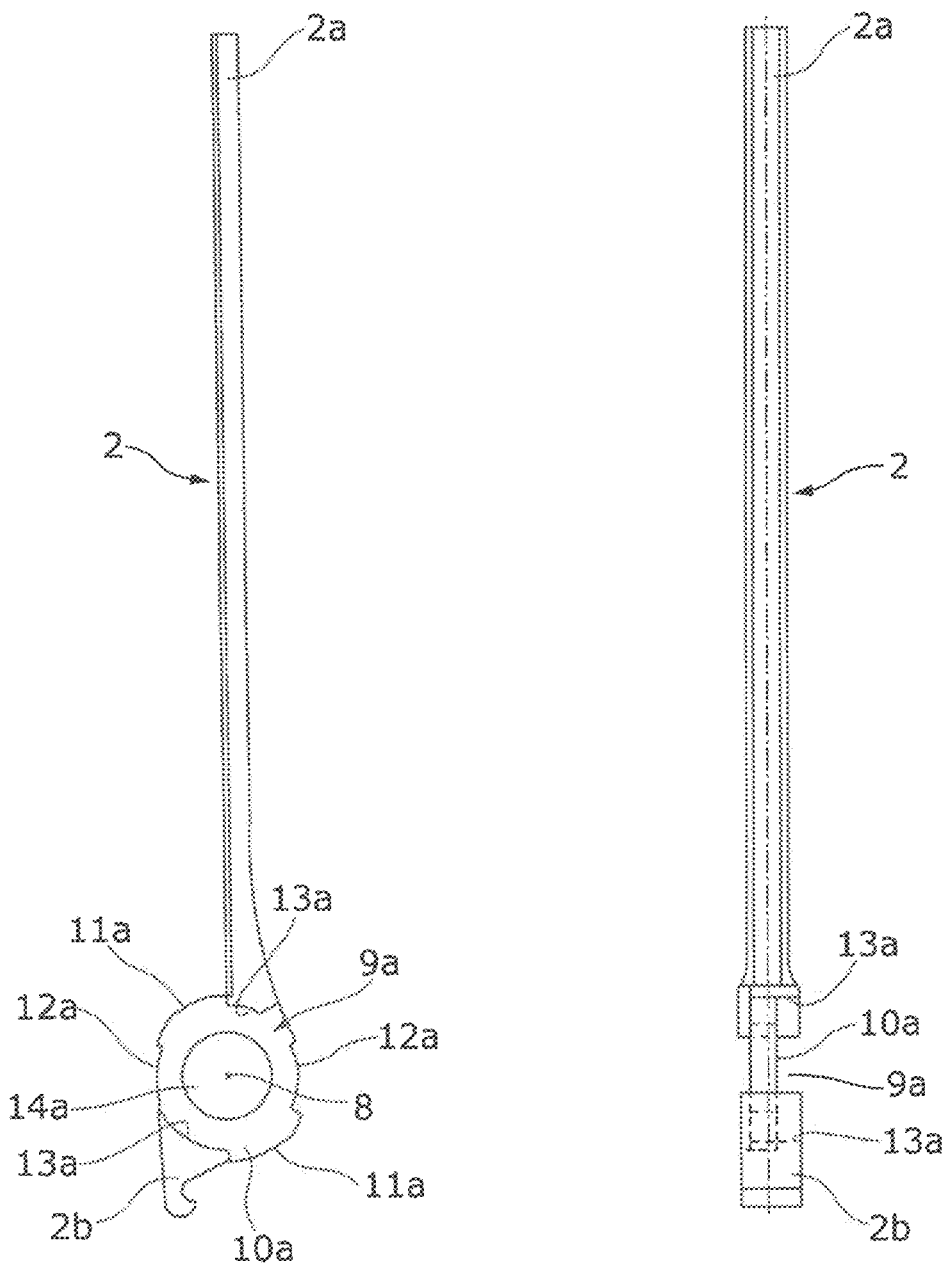
FIGS. 2a, 2b show a first clip part of the clip shown in FIG. 1 in a plan view (FIG. 2a) and in a lateral view (FIG. 2b)

As is shown in FIGS. 2a, 2b, the one, first clip part 2 has a clamping arm 2a and an operating arm 2b which in relation to the rotation axis 8 are mutually opposite, and therebetween a rotary bearing portion 9a. The rotary bearing portion 9a is configured as an axially open plug receptacle, the base or the base plate 10a, respectively, thereof being configured so as to be annular and on the external circumference having two mutually opposite external rotary guide portions 11a and therebetween in each case one assembly recess 12a that is recessed in a radially inward manner. Two internal rotary guide portions 13a which in relation to the rotation axis 8 mutually opposite and face the rotation axis 8 and which are in each case formed by one shoulder on the clamping arm 2a and on the operating arm 2b are provided on the transition from the base plate 10a to the clamping arm 2a, or to the operating arm 2b, respectively. An opening 14a that is centric in relation to the rotation axis 8 is provided in the base plate 10a.

As is shown in FIGS. 3a, 3b, the other, second clip part 3 has a clamping arm 3a and an operating arm 3b which in relation to the rotation axis 8 are mutually opposite, and therebetween a rotary bearing portion 9b. The rotary bearing portion 9b is configured as an axially open plug receptacle, the base or the base plate 10b, respectively, thereof being configured so as to be annular and on the external circumference having two mutually opposite external rotary guide portions 11b and therebetween in each case one assembly recess 12b that is recessed in a radially inward manner. Two internal rotary guide portions 13b which in relation to the rotation axis 8 mutually opposite and face the rotation axis 8 and which are in each case formed by one shoulder on the clamping arm 3a and on the operating arm 3b are provided on the transition from the base plate 10b to the clamping arm 3a, or to the operating arm 3b, respectively. An opening 14b that is centric in relation to the rotation axis 8 is provided in the base plate 10b. The internal rotary guide portions 13b on that side that is opposite the base plate 10b are in each case overreached by a projection 15 and on account thereof configured as a guide groove. With the exception of the two projections 15 thereof, the second clip part 3 is configured in a manner identical to that of the first clip part 2.

In order for the two clip parts 2, 3 to be connected to form the surgical clip 1, the clip parts 2, 3 by way of the two assembly clearances 12a or 12b, respectively, thereof are in each case aligned between the two external rotary guide portions 11b or 11a, respectively, of the respective other clip part and are axially plug-fitted into one another until the base plates 10a, 10b of the clip parts 2, 3 abut one another. The two clip parts 2, 3 are subsequently rotated in the direction towards the closed end position shown in FIG. 1, on account of which the external rotary guide portions 11a of the first clip part 2 engage in the guide grooves 13b of the second clip part 3 and are rotatably mounted therein, and the external rotary guide portions 11b of the second clip part 3 are also rotatably mounted on the internal rotary bearing portions 13a of the first clip part 2. On account of the engagement of the external rotary guide portions 11a in the guide grooves 13b, the two clip parts 2, 3 are axially interconnected, or locked counter to the plug-fitting direction, respectively.

The centric opening 14a, 14b of the interconnected clip parts 2, 3 form a passage opening 16 in which the leg spring 4 by way of the spring coilings is 7 thereof is disposed. The two spring legs 17 of the leg spring 4 at 18 are connected in a materially integral manner to the base plates 10a, 10b of the two clip parts 2, 3 by ultrasonic welding and, on account thereof, supported on the two clip parts 2, 3. With the aid of an applying forceps that engage between the two operating arms 2b, 3b, the operating arms 2b, 3b can be forced apart counter to the force of the leg spring 4 and, on account thereof, the clamping arms 2a, 3a can be opened.

Instead of the plug/rotary-fit mounting shown in FIGS. 1 to 3, the two clip parts 2, 3 can be mutually rotatably mounted in a direct or indirect manner in any other way, thus for example by way of a tongue-and-groove mounting as in FIGS. 12 to 16 of DE 10 2004 016 859 A1, by way of a latching or snap-fit rotary mounting such as in DE 103 09 491 B4, by way of the leg spring 4 as in DE 199 35 418 C2, or by way of a bearing sleeve that is molded thereon or a separate, as in DE 10 2013 200 127 A1.

Various variants of supporting the two spring legs 17 on an axially projecting protrusion 19 of the clip parts 2, 3 are shown in FIGS. 4a-4e. The protrusion 19 is integrally molded on the clip parts 2, 3 and is thus likewise formed from PEEK that is reinforced with short carbon fibers 5. The protrusion 19 is preferably molded externally on the rotary bearing portion 9a, 9b, thus on the base plate 10a, 10b, but can alternatively also be molded on the clamping arm 2a, 3a, or on the operating arm 2b, 3b. The spring leg 17 is supported on the protrusion 19 at least in the force direction 20 of the spring effect of said spring leg 17.

Figure 4A:
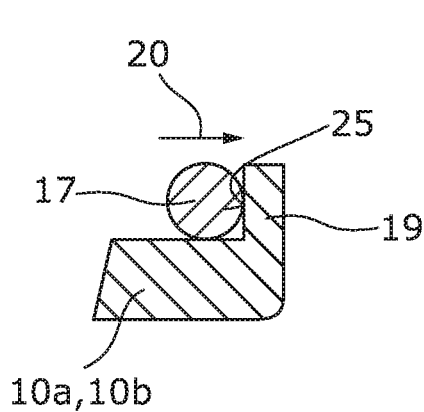
FIGS. 4a-4e show various modifications of a protrusion for supporting the leg spring, said protrusion being in each case present on the clip parts.

The spring leg 17 in FIG. 4a is supported on an end face 25 of the protrusion 19 facing in the force direction 20 or in the rotation direction of the clip 1, respectively, but is not axially fixed.

Figure 4B:
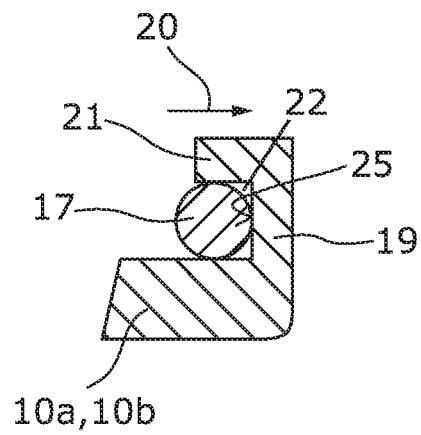

The protrusion 17 in FIG. 4b is configured so as to be hook-shaped having a projection 21 and thus configured having a groove 22 that is open counter to the force direction 20, the spring leg 17 being placed in said groove 22 and, because of being axially overreached, being axially fixed. Here, the groove base forms an end face 25 of the protrusion 19 facing in the force direction 20 or in the rotation direction of the clip 1, respectively, for supporting the spring leg 17.

Figure 4C:
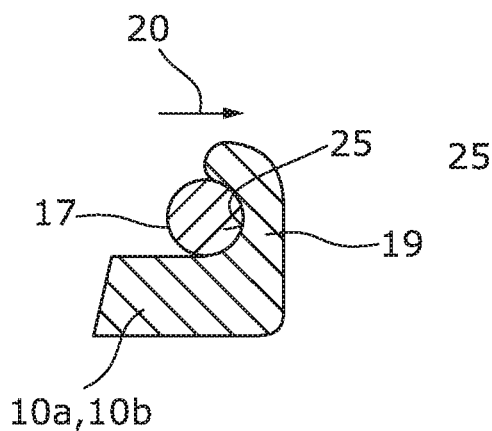

The spring leg 17 in FIG. 4c is in part encompassed in a form-fitting manner by the protrusion 19 and, on account thereof, is axially fixed. For example, the protrusion 19 can have been molded or deformed, respectively, around the spring leg 17 by way of a heat treatment. Here, the spring leg 17 is supported on an inner end face 25 of the protrusion 19 facing in the force direction 20 or in the rotation direction of the clip 1, respectively.

Figure 4D:
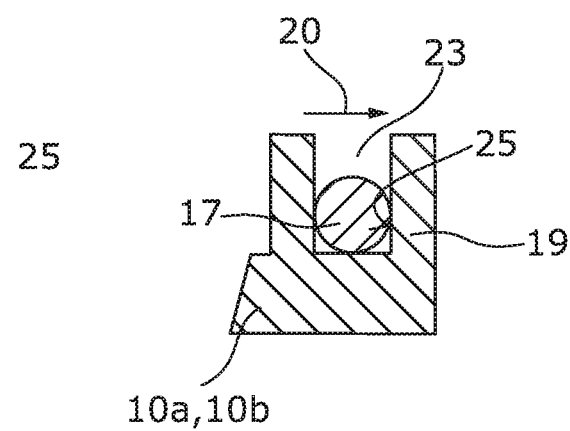

The protrusion 19 in FIG. 4d has a slot 23 which is open axially towards one side, in which the spring leg 17 is placed and, on account thereof, is supported in and counter to the direction 20 of the spring effect of said spring leg 17. Here, one of the two slot sides (in FIG. 4d the right one) forms an end face 25 of the protrusion 19 facing in the force direction 20 or in the rotation direction of the clip 1, respectively, for supporting the spring leg 17.

Figure 4E:
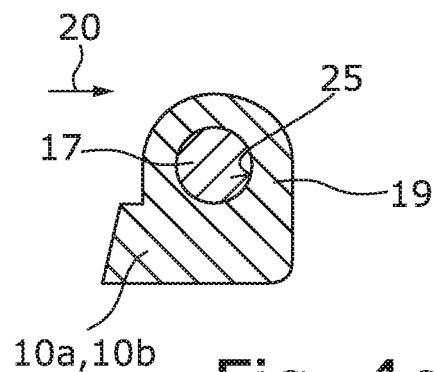

The spring leg 17 in FIG. 4e is completely embedded or melted, respectively, in a form-fitting manner in the protrusion 19. For example, the protrusion 19 can initially have a slot that is open towards one side, the open slot end thereof being melted by a heat treatment and, on account thereof being closed, once the spring leg 17 has been placed into the slot. Here, the spring leg 17 is supported on an inner face 25 of the protrusion 19 facing in the force direction 20 or in the rotation direction of the clip 1, respectively.

The surgical clip 1 shown in FIGS. 1 to 4 is thus formed completely from carbon-fiber-reinforced PEEK, thus from an X-ray-transparent material.

Figure 5A:
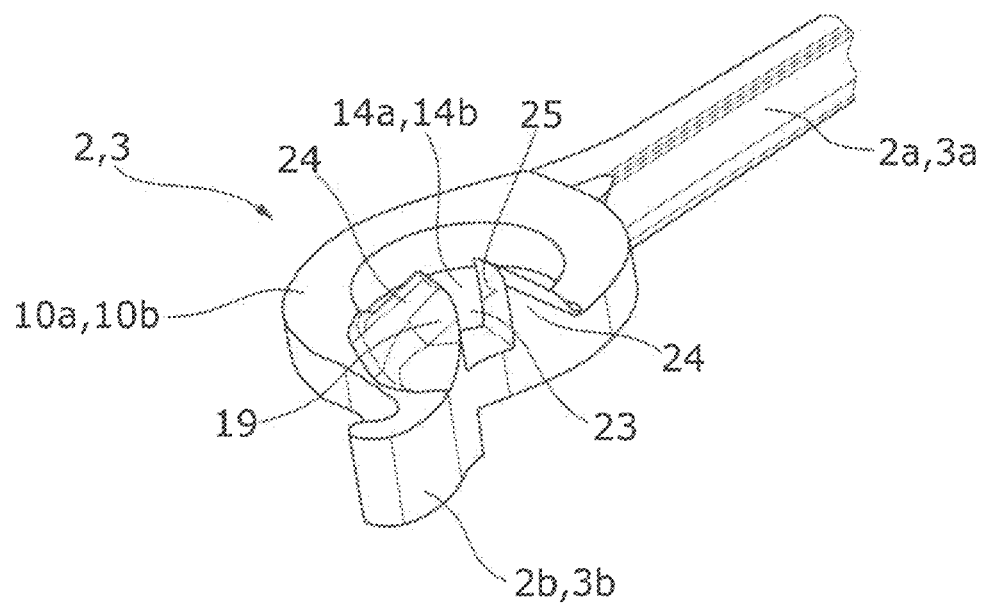
FIGS. 5a, 5b show a further exemplary embodiment of a first or second clip part having a ramp-shaped protrusion, in a perspective view (FIG. 5a) and in a fragmented lateral view (FIG. 5b).
Figure 5B:
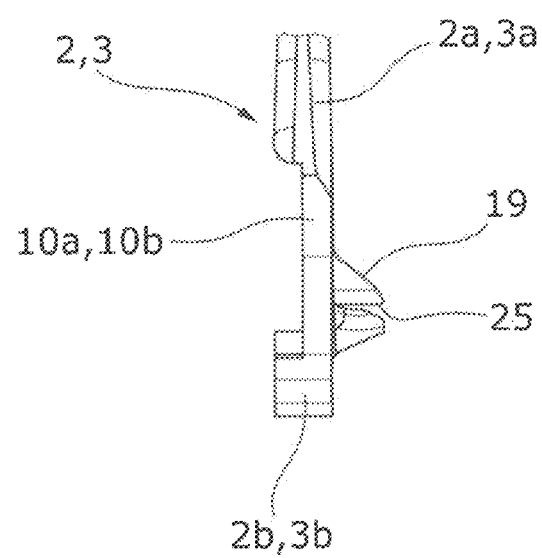

The clip part 2, 3 shown in FIGS. 5a, 5b here serves as a first as well as a second clip part. That is to say that the clip is assembled from two clip parts 2, 3 of identical construction. The protrusion 19 is configured as in FIG. 4d, having a slot 23 that is axially open towards one side, the two side walls 24 of said slot 23 being in each case configured as a ramp that ascends towards the slot 23. Here, one of the two side walls 24 forms an end face 25 of the protrusion 19 facing in the force direction 20 or in the rotation direction of the clip 1 respectively, for supporting the spring leg 17.

What is claimed is:

1. A surgical clip, comprising:
   two clip parts which are rotatably interconnected about a rotation axis and a leg spring, the leg spring having a spring coiling and two spring legs,
   each of the two spring legs respectively being supported on one of the two clip parts so as to mutually pretension the two clip parts;
   wherein the leg spring is formed from a plastics material that is reinforced with continuous carbon fibers, wherein the continuous carbon fibers are aligned along the spring coilings of the leg spring;
   wherein the two clip parts have in each case a passage opening in which the spring coiling is disposed; and
   wherein the two clip parts have in each case one protrusion which axially projects in a direction of the rotation axis and on which the respective spring leg of the leg spring is supported, wherein the protrusion is integrally molded externally on the clip part.

2. The surgical clip according to claim 1, wherein the plastics material of the leg spring is PEEK.

3. The surgical clip according to claim 2, wherein the two clip parts are formed from a plastics material.

4. The surgical clip according to claim 3, wherein the plastics material of the two clip parts is PEEK.

5. The surgical clip according to claim 3, wherein the plastics material of the two clip parts is reinforced with short carbon fibers.

6. The surgical clip according to claim 1, wherein the two spring legs of the leg spring are connected to the two clip parts in a materially integral manner of being welded to one another.

7. The surgical clip according to claim 1, wherein the protrusion is configured so as to be hook-shaped and reaches radially across the respective spring leg.

8. The surgical clip according to claim 1, wherein the respective spring leg is at least partially embedded in the protrusion in a form-fitting manner of being melted therein.

9. The surgical clip according to claim 1, wherein the two clip parts have in each case one clamping arm, one operating arm, and a rotary bearing portion located there between, said rotary bearing portion having an opening, wherein the rotary bearing portions of the two clip parts are mounted so as to be rotatable within one another, and the openings of the two clip parts form an axial passage opening in which at least some of the spring coilings of the leg spring are disposed.

10. The surgical clip according to claim 1, wherein the spring leg is supported on an end face or inner face of the protrusion facing in the force direction of the leg spring or in the rotation direction of the clip, respectively.

* * * * *